United States Patent [19]

Aoki et al.

[11] 4,327,173
[45] Apr. 27, 1982

[54] COLOR PHOTOGRAPHIC LIGHT-SENSITIVE MATERIAL

[75] Inventors: Kozo Aoki; Yoshio Seoka; Yukio Yokota, all of Minami-ashigara, Japan

[73] Assignee: Fuji Photo Film Co., Ltd., Kanagawa, Japan

[21] Appl. No.: 227,908

[22] Filed: Jan. 23, 1981

[30] Foreign Application Priority Data

Jan. 23, 1980 [JP] Japan ..................... 55-6512

[51] Int. Cl.$^3$ ......................... G03C 1/76; G03C 1/40
[52] U.S. Cl. ................................. 430/505; 430/552; 430/553; 430/558
[58] Field of Search ................ 430/552, 553, 558, 505

[56] References Cited

U.S. PATENT DOCUMENTS

| | | | |
|---|---|---|---|
| 2,886,436 | 5/1959 | Schmidt et al. | 430/558 |
| 3,617,291 | 11/1971 | Sawdeg | 430/558 |
| 4,078,936 | 3/1978 | Masuda et al. | 430/558 |
| 4,233,399 | 11/1980 | Kitzing et al. | 430/558 |

*Primary Examiner*—J. Travis Brown
*Attorney, Agent, or Firm*—Sughrue, Mion, Zinn, Macpeak and Seas

[57] ABSTRACT

A color photographic light-sensitive material is described containing a cyan dye forming coupler represented by formula (I)

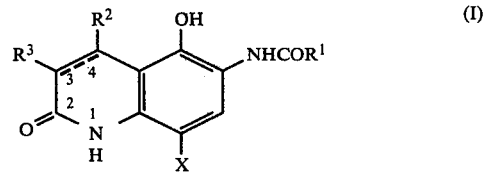

wherein $R^1$ represents a substituted or unsubstituted alkyl group or a substituted or unsubstituted aryl group; $R^2$ and $R^3$ each represents hydrogen, a halogen atom, an alkyl group, an aryl group, an alkoxy group, an alkoxycarbonyl group, an alkylcarbonyl group, an arylcarbonyl group, an alkylcarbamoyl group, an arylcarbamoyl group wherein said groups may be substituted or unsubstituted, or a nitryl group; and X represents hydrogen or a coupling-off group; also a double bond may be formed between the carbon atom at the 3-position and the carbon atoms at the 4-position.

The color photographic light-sensitive material provides color images having excellent fastness to light and heat.

17 Claims, No Drawings

COLOR PHOTOGRAPHIC LIGHT-SENSITIVE MATERIAL

BACKGROUND OF THE INVENTION

The present invention relates to a color photographic light-sensitive material containing a novel cyan dye forming coupler.

When an imagewise exposed silver halide photographic light-sensitive material is subjected to color development processing, an oxidation product of the aromatic primary amine developing agent reacts with a dye forming coupler to form a color image.

Usually, a color-reproducing process based on subtractive color photography is relied upon forming yellow, magenta, and cyan color images, the colors of which are in complementary relationship with the exposure to blue, green, and red light, respectively. For example, phenol derivatives or naphthol derivatives are used as couplers for forming cyan color images.

However, the color images formed from conventionally employed phenol derivatives or naphthol derivatives have some problems in view of the durability thereof. For example, color images formed from the 2-acylaminophenol cyan couplers as described in U.S. Pat. Nos. 2,367,531 and 2,423,730 are generally inferior the fastness to heat, color images formed from the 2,5-diacylaminophenol cyan couplers as described in U.S. Pat. Nos. 2,369,929 and 2,772,162 are generally inferior in the fastness to light, and color images formed from 1-hydroxy-2-naphthamide cyan couplers are generally inferior in fastness to both light and heat.

SUMMARY OF THE INVENTION

Therefore, it is an object of the present invention to improve the fastness of color images with respect to cyan dye forming couplers.

Another object of the present invention is to provide a color photographic light-sensitive material having good stability against both light and heat.

Still another object of the present invention is to provide a coupler which does not substantially decrease in optical density when a color photographic light-sensitive material containing the coupler is processed with a bleaching solution which has a weak oxidation power, for example, a bleach solution containing sodium iron (III) ethylenediamine tetraacetate or ammonium iron (III) ethylenediamine tetraacetate, etc. or a bleaching solution which is exhausted.

Other objects of the present invention will become apparent from the following detailed description and examples.

These objects of the present invention have been accomplished by using a coupler represented by formula (I)

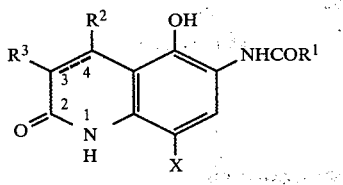

where $R^1$ represents a substituted or unsubstituted alkyl group or a substituted or unsubstituted aryl group; $R^2$ and $R^3$ (which may be the same or different) each represents hydrogen, a halogen atom, an alkyl group, an aryl group, an alkoxy group, an alkoxycarbonyl group, an alkylcarbonyl group, an arylcarbonyl group, an alkylcarbamoyl group, an arylcarbamoyl group, wherein said groups may be substituted or unsubstituted, or a nitryl group, or $R^2$ and $R^3$ together represent a double bond between the 3-position and 4-position carbon atoms; X represents hydrogen or a coupling-off group (i.e., a group capable of being released upon an oxidation coupling reaction with an oxidation product of a developing agent); and the bond between the carbon atom at the 3-position and the carbon atom at the 4-position can be a single or double bond.

DETAILED DESCRIPTION OF THE INVENTION

Preferred embodiments of $R^1$, $R^2$, $R^3$, and X in the above general formula (I) will now be described in greater detail below.

In formula (I), $R^1$ can represent a straight chain or branched chain, or cyclic, alkyl group, preferably an alkyl group having from 1 to 22 carbon atoms (for example, a methyl group, an ethyl group, a butyl group, a hexyl group, a tridecyl group, a pentadecyl group, a heptadecyl group, a cyclohexyl group, a norbornyl group, an adamantyl group, etc.), or an aryl group (for example, a phenyl group, a naphthyl group, etc.). These groups can be substituted with one or more substituents selected from an alkyl group, a halogen atom, a nitrogen group, a cyano group, an aryl group (for example, a phenyl group, a naphthyl group, etc.), an alkoxy group (for example, a methoxy group, an ethoxy group, a methoxyethoxy group, a 2-ethylhexyloxy group, etc.), an aryloxy group (for example, a phenoxy group, a 4-hydroxyphenoxy group, a 2,4-di-tert-amylphenoxy group, a naphthoxy group, etc.), a carboxy group, an alkylcarbonyl group (for example, an acetyl group, a tetradecanoyl group, etc.), an arylcarbonyl group (for example, a benzoyl group, etc.), an alkoxycarbonyl group (for example, a methoxycarbonyl group, a benzyloxycarbonyl group, etc.), an aryloxycarbonyl group (for example, a phenoxycarbonyl group, a p-tolyloxycarbonyl group, etc.), an acyloxy group (for example, an acetyloxy group, a tetradecanoyl group, a benzoyl group, etc.), a sulfamoyl group (for example, an N-ethylsulfamoyl group, an N-octadecylsulfamoyl group, etc.), a carbamoyl group (or example, an N-ethylcarbamoyl group, an N-methyl-N-dodecylcarbamoyl group, etc.), an acylamino group (for example, an acetylamino group, a benzamino group, etc.), a diacylamino group (for example, a succinimido group, a hydantoinyl group, etc.), a ureido group (for example, a methylureido group, a phenylureido group, etc.), a sulfonamido group (for example, a methanesulfonamido group, dodecansulfonamido group, a methoxyethanesulfonamido group, etc.) and a hydroxy group. When the alkyl group is substituted with fluorine atoms, it may be a so-called polyfluoroalkyl group.

In formula (I), $R^2$ and $R^3$ (which may be the same or different) each represents hydrogen, a halogen atom, a straight chain or branched chain or cyclic alkyl group, preferably an alkyl group having from 1 to 22 carbon atoms (for example, a methyl group, an ethyl group, a butyl group, a heptadecyl group, a cyclohexyl group, etc.), an aryl group (for example, a phenyl group, a naphthyl group, etc.), an alkoxy group (for example, a methoxy group, a propyloxy group, a dodecyloxy group, etc.), an alkoxycarbonyl group (for example, a methoxycarbonyl group, a tetradecyloxycarbonyl group, a benzyloxycarbonyl group, etc.), an alkylcarbonyl group (for example, an acetyl group, a tetradecanoyl group, etc.), an arylcarbonyl group (for example, a benzoyl group, etc.), an alkylcarbamoyl group (for example, a methylcarbamoyl group, a butylcarbamoyl group, a tetradecylcarbamoyl group, etc.), an arylcarbamoyl group (for example, a phenylcarbamoyl group, etc.), or a nitryl group. The alkyl and aryl groups may be substituted with one or more of the substituents for $R_1$ described above.

In the general formula (I), X represents hydrogen or a coupling-off group. Examples of the coupling-off groups include, for example, a halogen atom (for example, a chlorine atom, etc.), an alkoxy group (for example, an ethoxy group, a dodecyloxy group, a methoxyethylcarbamoylmethoxy group, a carboxymethoxy group, a methylsulfonamidoethoxy group, an ethylsulfonylethoxy group, etc.), an aryloxy group (for example, a phenoxy group, a naphthoxy group, etc.), an acyloxy group (for example, an acetoxy group, a tetradecanoyloxy group, a benzoyloxy group, etc.), a sulfonyloxy group (for example, a methanesulfonyloxy group, a dodecansulfonyloxy group, etc.), an acylamino group (for example, a dichloroacetylamino group, a heptafluorobutyrylamino group, etc.), a sulfonylamino group (for example, a methanesulfonylamino group, a dodecanesulfonylamino group, a benzenesulfonylamino group, etc.), an alkoxycarbonyloxy group (for example, an ethoxycarbonyloxy group, a benzyloxycarbonyloxy group, etc.), an aryloxycarbonyloxy group (for example, a phenoxycarbonyloxy group, etc.), an imido group (for example, a succinimido group, a hydantoinyl group, etc.), and the like.

In formula (I), an alkyl group having from 8 to 22 carbon atoms and an aryl group having from 8 to 22 carbon atoms are particularly preferred for $R^1$, an alkyl group and a substituted phenyl group are particularly preferred for $R^2$, hydrogen and a halogen atom are particularly preferred for $R^3$, and hydrogen and a chlorine atom are particularly preferred for X.

Examples of the couplers included in the scope of the present invention are set forth below, but the present invention is not to be construed as being limited thereto.

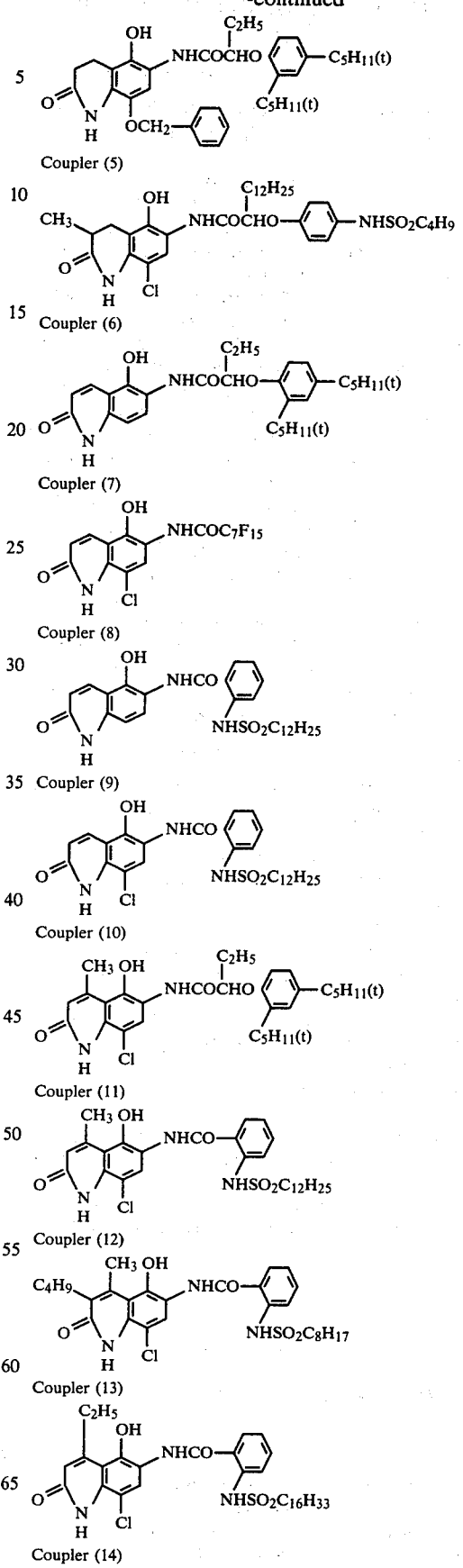

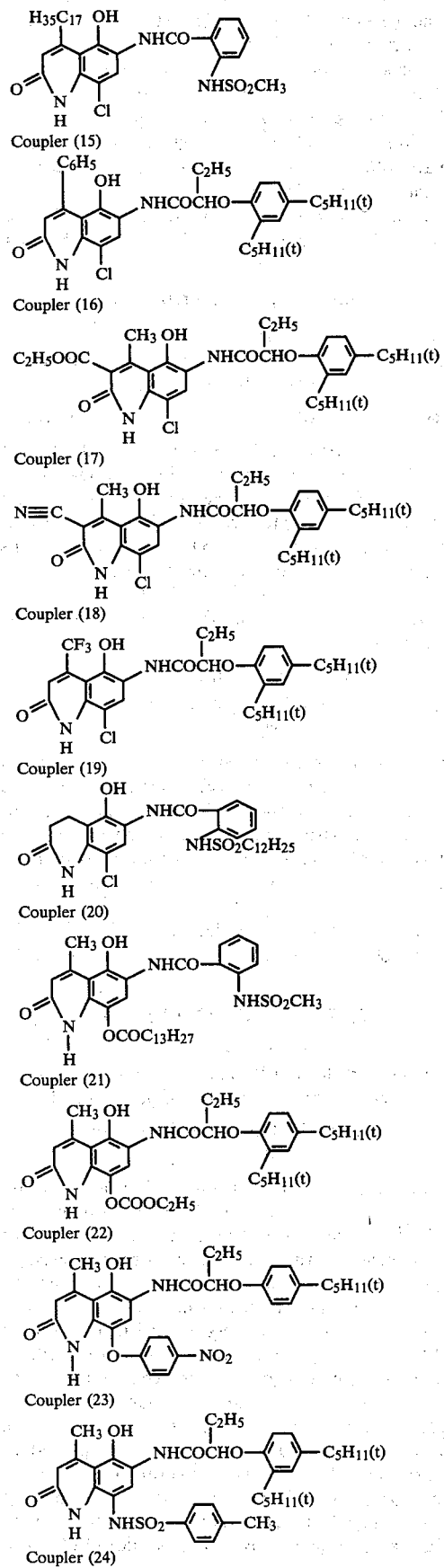

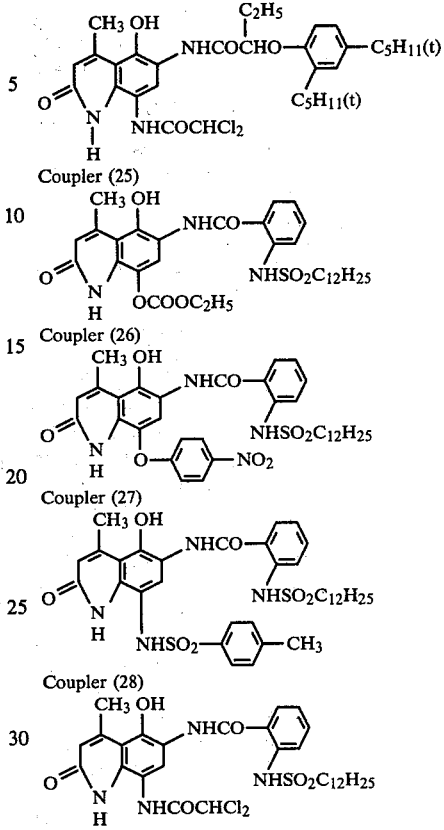

The couplers which can be used in the present invention can be generally synthesized in the following manner. 5-hydroxycarbostyryl and 5-hydroxy-3,4-dihydrocarbostyryl which are parent nuclei, can be synthesized by the methods described, for example, in *Ber.*, Vol. 20, page 2174, *Chem. Ind.* (London), Vol. 1970, page 1435, Japanese Patent Publication Nos. 39694/71 and 39695/71, *Yakugakuzasshi*, Vol. 96, page 571 (1976), etc. Also, these parent nuclei can be synthesized by the methods described in *J. Am. Chem. Soc.*, Vol. 70, page 2402 (1948) and *Org. Synth.*, Coll. Vol. 3, page 374 (1955).

The couplers can be synthesized by introducing a coupling-off group into the 4-position by means of halogenation, acylation by applying an acid halide to a hydroxy group and an amino group, or etherification by applying an alkyl halide or an aryl halide to a hydroxy group, and by introducing an acylamino group into the 2-position by means of nitration, reduction, and reaction with acid chloride in a starting material for the parent nuclei or after synthesis of the parent nucleus.

Representative synthesis examples of the couplers according to the present invention are specifically set forth below.

SYNTHESIS EXAMPLE 1

Synthesis of 6-[2-(2,4-Di-tert-amylphenoxy)butanamido]-5-hydroxy-3,4-dihydrocarbostyryl [Coupler (1)]

Step (i): Synthesis of 5-Hydroxy-6-nitro-3,4-dihydrocarbostyryl 25 g of 5-hydroxy-3,4-dihydrocabostyryl was dissolved in 110 ml of acetic anhydride, and to the solution was added dropwise at 5° C. a mixture of 12 g of fuming nitric acid and 75 ml of acetic acid. The reaction mixture was stirred at 5° C. for 2 hours and 20 g of ice was added thereto. The crystals deposited were collected by filtration and suspended in a 3 N aqueous sodium hydroxide solution. After filtration the filtrate was neutralized with hydrochloric acid and the crystals deposited were collected by filtration and washed with water. After drying, 22 g of the 5-hydroxy-6-nitro-3,4-dihydrocarbostyryl compound was obtained.

Step (ii): Synthesis of 6-[2-(2,4-Di-tert-amylphenoxy)butanamido]-5-hydroxy-3,4-dihydrocarbostyryl To 22 g of the 5-hydroxy-6-nitro-3,4-dihydrocarbostyryl were added 100 ml of acetone and 16.3 ml of triethylamine and then added dropwise 37.7 g of 2-(2,4-di-tert-amylphenoxy)butanoyl chloride at room temperature. After stirring for 1 hour at room temperature, 100 ml of ethyl acetate was added to the reaction mixture. The triethylamine hydrochloride deposited was removed by filtration. The filtrate was concentrated under reduced pressure and crystallized from hexane to obtain 34 g of crystals having a melting point of 101° to 105° C. To the crystals were added 150 ml of acetic acid, 70 ml of ethanol, and 30 ml of water, and then 32 g of reduced iron was added little by little while refluxing. After refluxing for 1 hour, the reaction mixture was poured into water and extracted with ethyl acetate. After washing with water, the solvent was distilled off under reduced pressure. By crystallization with acetonitrile 26 g of the desired coupler having a melting point of 203° to 205° C. was obtained.

Elemental Analysis: Calculated: C: 72.47%, H: 8.39%, N: 5.83%. Found: C: 72.45%, H: 8.45%, N: 5.65%.

SYNTHESIS EXAMPLE 2

Synthesis of 6-[2-(2,4-Di-tert-amylphenoxy)butanamido]-8-benzyloxy-5-hydroxy-3,4-dihydrocarbostyryl [Coupler (4)]

Step (i): Synthesis of 8-Benzyloxy-5-hydroxy-6-nitro-3,4-dihydrocarbostyryl 28 g of 5,8-dihydroxy-3,4-dihydrocarbostyryl was dissolved in 1 liter of acetone and to the solution were added 25 g of benzyl chloride, and then a solution containing 24 g of potassium carbonate dissolved in 300 ml of water. After refluxing for 3 hours, acetone was distilled off to deposit crystals. The residue was acidified with hydrochloric acid, and the crystals were collected by filtration. The crystals were suspended in 450 ml of a 10% aqueous sodium hydroxide solution. After filtration, the filter was acidified and the crystals deposited were collected to yield 18.2 g.

The crystals were suspended in 300 ml of hexane and 7.6 ml of nitric acid was added dropwise while cooling with water for 2 hours. After stirring for 1 hour the crystals were collected, washed with hexane and then with water. After drying 12.5 g of the 8-benzyloxy-5-hydroxy-6-nitro-3,4-dihydrocarbylstyryl compound having a melting point of 185° to 190° C. was obtained.

Step (ii): Synthesis of 6-[2-(2,4-Di-tert-amylphenoxy)butanamido]-8-benzyloxy-5-hydroxy-3,4-dihydrocarbostyryl To 12 g of the 8-benzyloxy-5-hydroxy-6-nitro-3,4-dihydrocarbostyryl, were added 30 ml of ethanol and 100 ml of water. Then 30 g of sodium hydrosulfite was added during refluxing thereof. After cooling, the crystals were collected by filtration to yield 8 g. 7.8 g of the crystals and 100 ml of acetonitrile were refluxed and 10 g of 2-(2,4-di-tert-amylphenoxy)butanoyl chloride was added dropwise thereto. After further refluxing for 2 hours, the solvent was distilled off under reduced pressure. The residue was separated by column chromatography (using silica gel and a solvent mixture of ethyl acetate and chloroform as a spreading agent) to obtain 15 g of the solid coupler.

Elemental Analysis: Calculated: C: 73.69%, H: 7.90%, N: 4.78%. Found: C: 73.71%, H: 7.98%, N: 4.92%.

SYNTHESIS EXAMPLE 3

Synthesis of 6-[2-(2,4-Di-tert-amylphenoxy)butanamido]-5-hydroxycarbostyryl [Coupler (6)]

Step (i): Synthesis of 5-Hydroxy-6-nitrocarbostyryl

To 10 g of 5-hydroxycarbostyryl was added 80 ml of acetic acid and then 6 ml of nitric acid was added dropwise under cooling with water thereto. After stirring for 1 hour, 100 ml of water was added and the crystals deposited were collected by filtration. The crystals were separated by a column chromatography (using silica gel and a solvent mixture of ethyl acetate and methanol) to obtain 7 g of the 5-hydroxy-6-nitrocarbostyryl compound.

Step (ii): Synthesis of 6-[2-(2,4-Di-tert-amylphenoxy)butanamido]-5-hydroxycarbostyryl The compound obtained in Step (i) above was reacted with 2-(2,4-di-tert-amylphenoxy)butanoyl chloride in the presence of acetone and triethylamine and the product was reduced with acetic acid and iron in the same manner as described in Synthesis Example 1 to obtain 12 g of the coupler, having a melting point of 231° to 235° C.

Elemental Analysis: Calculated: C: 72.77%, H: 8.00%, N: 5.85%. Found: C: 72.93%, H: 8.04%, N: 5.99%.

SYNTHESIS EXAMPLE 4

Synthesis of 8-Chloro-6-(2-dodecansulfonamidobenzoylamino)-5-hydroxy-4-methylcarbostyryl [Coupler (11)]

Step (i): Synthesis of 2-Dodecansulfonamidobenzoyl chloride

To a mixture of 90.6 g of anthranilic acid methyl ester, 85 g triethylamine, and 500 ml of toluene was added 107.5 g of dodecansulfonic acid at 15° C. After stirring for 2 hours, the reaction mixture was washed with diluted hydrochloric acid and then a saturated aqueous sodium chloride solution. The solvent was distilled off under reduced pressure and to the residue were added 500 ml of methanol and a solution containing 64 g of sodium hydroxide dissolved in 100 ml of water. The mixture was heated for 1 hour while stirring and 1 liter of water was added thereto. The pH of the mixture was adjusted to 4 with hydrochloric acid to deposit crystals. The crystals were collected by filtration and recrystallized from acetonitrile to obtain 99 g of carboxylic acid. Then to this compound there were added 500 ml of benzene and 48 g of thionyl chloride and the mixture was refluxed for 2 hours. By distilling off the solvent and the excess thionyl chloride under reduced pressure, 103 g of 2-dodecansulfonamidobenzoyl chloride was obtained.

Step (ii): Synthesis of 5-Amino-4-chloro -2-(2-dodecansulfonamidobenzoylamino)phenol 28.2 g of 2-amino-4-chloro-5-nitrophenol was refluxed in 150 ml of acetonitrile and to the mixture, a solution containing 52.7 g of 2-dodecansulfonamidobenzoyl chloride obtained in Step (i) above dissolved in 50 ml of acetonitrile was added. After refluxing for 4 hours, the reaction mixture was cooled to deposit crystals. The crystals were collected by filtration, washed with acetonitrile, and dried to yield 56 g thereof. These crystals were refluxed with stirring for 1 hour together with 60 g of reduced iron powder, 2 g of ammonium chloride, 50 ml of water, and 500 ml of isopropanol. After removing the iron powder by filtration, the filtrate was poured into 2 liters of water to deposit crystals. The crystals were collected by filtration and recrystallized from acetonitrile to obtain 36 g of the 5-amino-4-chloro-2-(2-dodecansulfonamidobenzoylamino)phenol compound.

Step (iii): Synthesis of 8-Chloro-6-(2-dodecansulfonamidobenzoylamino)-5-hydroxy-4-methylcarbostyryl 36 g of the 5-amino-4-chloro-2-(2-dodecansulfonamidobenzoylamino)phenol obtained in Step (ii) above was dissolved in 7.3 g pyridine and 200 ml of acetonitrile, and to the solution, 7.2 g of diketene were added dropwise. The mixture was heated with stirring for 4 hours and then cooled to deposit the crystals. The crystals were collected by filtration, washed with acetonitrile and dried to yield 33.5 g. 22.5 g of the crystals were added to 200 ml of concentrated sulfuric acid to dissolve and the solution was heated at 40° to 45° C. and stirred for 2 hours. The reaction mixture was poured into 1 liter of ice water. The mixture was neutralized with 250 g of sodium hydroxide and the crystals thus deposited were collected by filtration and recrystallized from acetone to obtain 6 g of the desired coupler, having a melting point of 170° to 173° C.

Elemental Analysis: Calculated: C: 60.47%, H: 6.60%, N: 7.30%. Found: C: 60.51%, H: 6.58%, N: 7.26%.

SYNTHESIS EXAMPLE 5

Synthesis of 6-[2-(2,4-Di-tert-amylphenoxy)butanamido]-8-chloro-5-hydroxy-4-phenylcarbostyryl [Coupler (15)]

Step (i): Synthesis of 8-Chloro-5-hydroxy-4-phenylcarbostyryl 28.8 g of ethyl benzoylacetate and 14.3 g of 3-amino-4-chlorophenol were heated at 140° C. for 8 hours. To the reaction mixture there was added 150 ml of acetonitrile, and the crystals thus deposited were collected by filtration to yield 25.3 g. 17 g of the crystals were added to 35 ml of concentrated sulfuric acid to dissolve and the solution was heated at 35° C. for 2 hours with stirring. The reaction mixture was poured into 500 ml of ice water. The mixture was neutralized with 24 g of sodium hydroxide and the crystals thus deposited were collected by filtration and washed with acetonitrile to obtain 9.5 g of the 8-chloro-5-hydroxy-4-phenylcarbostyryl compound.

Step (ii): Synthesis of 6-[2-(2,4-Di-tert-amylphenoxy)butanamido]-8-chloro-5-hydroxy-4-phenylcarbostyryl 8 g of the 8-chloro-5-hydroxy-4-phenylcarbostyryl obtained in Step (i) above was suspended in 50 ml of acetic acid and to the suspension, 2.0 ml of nitric acid was added dropwise. After stirring for 2 hours, the crystals were collected by filtration and washed with water to obtain 8 g of the nitro compound. 8 g of the nitro compound was suspended in a mixture of 100 ml of methanol and 150 ml of water and to the mixture, 30 g of sodium hydrosulfite was added while refluxing. After refluxing for 1 hour, the reaction mixture was poured into 500 ml of water and the crystals thus deposited were collected by filtration to yield 7.2 g. 7 g of the crystals were refluxed in 150 ml of acetonitrile and 9.1 g of 2-(2,4-di-tert-amylphenoxy)butanoyl chloride was added dropwise thereto. After refluxing for 4 hours, the reaction mixture was cooled, poured into water and extracted with ethyl acetate. The solvent was distilled off under reduced pressure, and the residue was separated by column chromatography (using silica gel and a solvent mixture of ethyl acetate and chloroform) to obtain 14 g of the desired coupler as an oily product.

Elemental Analysis: Calculated: C: 71.37%, H: 6.97%, N: 4.76%. Found C: 71.52%, H: 7.10%, N: 4.61%.

The coupler according to the present invention can be present in silver halide emulsion layers. The coupler according to the present invention, if desired, may be present in hydrophilic colloid layer adjacent to silver halide emulsion layer.

The photographic emulsion layer of the photographic light-sensitive material produced using the coupler according to the present invention can contain a dye-image-forming coupler (also referred to herein simply as a coupler) other than the coupler according to the present invention, that is, other compounds capable of forming a dye upon reaction with an oxidation product of an aromatic amine developing agent.

Non-diffusible couplers which contain a hydrophobic group, also referred to as a ballst group, in the molecule thereof are preferred as couplers. Couplers can be 4-equivalent or 2-equivalent couplers. In addition, colored couplers providing a colow correction effect, or couplers which release development inhibitors upon development (so-called DIR couplers) can also be present therein. Also, couplers which provide a colorless product on coupling can be employed.

Conventional open chain ketomethylene type couplers can be employed as yellow-color-forming couplers. Of these couplers, benzoyl acetanilide type and pivaloyl acetanilide type compounds are especially effective. Specific examples of yellow-color-forming couplers which can be employed are described, for example, in U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,219,917, 2,261,361 and 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77 and 115219/77.

Pyrazolone type compounds, indazolone type compounds, cyanoacetyl compounds, etc., can be employed as magenta-color-forming couplers, and particularly preferred couplers are pyrazolone type compounds. Specific examples of magenta-color-forming couplers which can be employed are those described, for example, in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German Patent Application (OLS) Nos. 2,408,665, 2,417,945, 2,418,959 and 2,424,467, Japanese Patent Publication No. 6031/65, Japanese Patent Application (OPI) Nos. 20826/76, 58922/77, 129538/74, 74027/74, 159336/75, 42121/77, 74028/74, 60233/75, 26541/76 and 55122/78.

Phenol type compounds, naphthol type compounds, etc., can be employed as cyan-color-forming couplers. Specific examples of cyan-color-forming couplers which can be employed are those described, for example, in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, German Patent Application (OLS) Nos. 2,414,830 and 2,454,329, Japanese Patent Application (OPI) Nos. 59838/73, 26034/76, 5055/73, 146828/76, 69624/77 and 90932/77.

Colored couplers which can be employed include those described, for example, in U.S. Pat. Nos. 3,476,560, 2,521,908 and 3,034,892, Japanese Patent Publication Nos. 2016/69, 22335/63, 11304/67 and 32461/69, Japanese Patent Application (OPI) Nos. 26034/76 and 42121/77, German Patent Application (OLS) No. 2,418,959.

DIR couplers which can be employed include those described, for example, in U.S. Pat. Nos. 3,227,554, 3,617,291, 3,701,783, 3,790,384 and 3,632,345, German Patent Application (OLS) Nos. 2,414,006, 2,454,301 and 2,454,329, British Patent 953,454, Japanese Patent Application (OPI) Nos. 69624/77, 122335/74, Japanese Patent Publication No. 16141/76.

In addition to DIR couplers, other compounds which release development inhibitors upon development can also be present in the light-sensitive material. For example, such DIR compounds as are described in U.S. Pat. Nos. 3,297,445 and 3,379,529, German Patent Application (OLS) No. 2,417,914, Japanese Patent Application (OPI) Nos. 15271/77 and 9116/78, etc., can be employed.

Two or more kinds of the couplers described above can be incorporated in the same layer, or the same coupler compound can also be present in two or more layers.

These couplers are incorporated into the emulsion layers, generally in an amount of from about $2 \times 10^{-3}$ mol to $5 \times 10^{-1}$ mol, preferably $1 \times 10^{-2}$ mol to $5 \times 10^{-1}$ mol, per mol of silver.

Conventional methods, e.g., the method described in U.S. Pat. No. 2,322,027, can be employed to incorporate the couplers into the silver halide emulsion layers. For example, the couplers can be dissolved in phthalic acid alkyl esters (e.g., dibutyl phthalate, dioctyl phthalate, etc.), phosphoric acid esters (e.g., diphenyl phosphate, triphenyl phosphate, tricresyl phosphate, dioctylbutyl phosphate), citric acid esters (e.g., tributyl acetylcitrate), benzoic acid esters (e.g., octyl benzoate), alkyl amides (e.g., diethyl laurylamide), fatty acid esters (e.g., dibutoxyethyl succinate, dioctyl azelate), etc.; or an organic solvent having a relatively low boiling point of from about 30° to 150° C. such as a lower alkyl acetate (e.g., ethyl acetate, butyl acetate, etc.), ethyl propionate, secbutyl alcohol, methyl isobutyl ketone, β-ethoxyethyl acetate, methyl Cellosolve acetate, etc. Then the solution is dispersed in a hydrophilic colloid. The above-described organic solvents having a high boiling point and the above-described organic solvents having a low boiling point may be used as mixtures, if desired.

Furthermore, the dispersing method using a polymeric material as described in Japanese Patent Publication No. 39853/76, Japanese Patent Application (OPI) No. 59943/76 can also be used.

When couplers having an acid group, such as a carboxylic acid group, a sulfonic acid group, etc., are used, they can be incorporated in a hydrophilic colloid as an alkaline aqueous solution thereof.

The hydrophilic colloid layers of the light-sensitive elements prepared in accordance with the present invention can also contain UV absorbents. For example, benzotriazole compounds substituted with aryl groups (e.g., those described in U.S. Pat. No. 3,533,794), 4-thiazolidone compounds (e.g., those described in U.S. Pat. Nos. 3,314,794 and 3,352,681), benzophenone compounds (e.g., those described in Japanese Patent Application (OPI) No. 2784/71), cinnamic acid ester compounds (e.g., those described in U.S. Pat. Nos. 3,707,375 and 3,705,805), butadiene compounds (e.g., those described in U.S. Pat. No. 4,045,229) or benzoxazole compounds (e.g., those described in U.S. Pat. No. 3,700,455) can be employed. Furthermore, the compounds as described in U.S. Pat. No. 3,499,762, Japanese Patent Application (OPI) No. 48535/79 can also be used. UV absorbing couplers (e.g., α-naphthol type cyan-color-forming couplers) and UV absorbing polymers can also be employed. These UV absorbents can also be mordanted in a specific layer(s), if desired.

The photographic emulsion used in this invention can be prepared using the methods described in, e.g., P. Glafkides, *Chimie et Physique Photographique*, Paul Montel, Paris (1967), G. F. Duffin, *Photographic Emulsion Chemistry*, The Focal Press, London (1966), V. L. Zelikman, et al., *Making and Coating Photographic Emulsions*, The Focal Press, London (1964), etc. That is, any of the acid method, the neutral method, the ammonia method and other methods can be used. Moreover, a soluble silver salt can be reacted with a soluble halogen salt using any of the single jet method, the double jet method, and a combination thereof.

A method in which grains are formed in the presence of an excess of silver ions (i.e., the so-called reverse mixing method) can also be used. As one of the modes of the double jet method, the method in which the pAg of the liquid phase in which the silver halide is to be produced is kept constant, that is, the so-called controlled double jet method, can be used. This method can provide silver halide emulsions having a regular crystal form and an almost uniform grain size.

Two or more silver halide emulsions which are separately prepared can be mixed and then used, if desired.

In the process of the formation of the silver halide grains or physical ripening, cadmium salts, zinc salts, lead salts, thallium salts, iridium salts or complex salts thereof, rhodium salts or complex salts thereof, iron salts or iron complex salts, and the like can be present.

Gelatin can advantageously be used as the binder or protective colloid for the photographic emulsion used in this invention. However, other hydrophilic colloids can be used as well. For example, proteins such as gelatin derivatives, graft polymers comprising gelatin and other high polymers, albumin, casein, etc.; cellulose derivatives such as hydroxyethyl cellulose, carboxy-methyl cellulose, cellulose sulfates, etc.; saccharide derivatives such as sodium alginate, starch derivatives, etc.; and various synthetic hydrophilic high polymers of homo- or copolymers such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc., can be used as the binder or protective colloid for the photographic emulsion.

Acid-processed gelatin and enzyme-processed gelatin as described in *Bull. Soc. Sci. Photo. Japan,* No. 16, p. 30 (1966) can be used as well as lime-processed gelatin as the gelatin component. In addition, the hydrolyzed products of gelatin and enzyme-decomposed products of gelatin are also suitable. Suitable gelatin derivatives which can be used include those obtained by reacting gelatin with various compounds, such as acid halides, acid anhydrides, isocyanates, bromoacetic acid, alkanesultones, vinylsulfonamides, maleinimides, polyalkylene oxides, epoxy compounds, etc. Specific examples thereof are described in U.S. Pat. Nos. 2,614,928, 3,132,945, 3,186,846, 3,312,553, British Pat. Nos. 861,414, 1,033,189, 1,005,784, Japanese Patent Publication No. 26845/67.

As the above-described gelatin graft polymer, those which are obtained by grafting homo- or copolymers of vinyl monomers such as acrylic acid, methacrylic acid, the ester or amide derivative thereof, acrylonitrile, styrene, etc., to gelatin can be used. In particular, graft polymers with a polymer having some compatibility with gelatin, such as polymers of acrylic acid, methacrylic acid, acrylamide, methacrylamide, hydroxyalkyl methacrylates, etc., are preferred. Examples thereof are described in U.S. Pat. Nos. 2,763,625, 2,831,767, 2,956,884, etc. Typical synthetic hydrophilic materials are described in, e.g., German Patent Application (OLS) No. 2,312,708, U.S. Pat. Nos. 3,620,751, 3,879,205 and Japanese Patent Publication No. 7561/68.

For the purpose of preventing fog or stabilizing the photographic properties during preparation, storage, and/or photographic processing of light-sensitive materials, a variety of compounds can be incorporated into photographic emulsions used according to the present invention. For example, a wide variety of compounds which are known as anti-fogging agents or stabilizers, such as azoles, e.g., benzothiazolium salts, nitrobenzimidazoles, nitroindazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (especially 1-phenyl-5-mercaptotetrazole), etc.; mercaptopyrimidines; mercaptotriazines; thioketo compounds, such as oxazolinethione; azaindenes, e.g., triazaindenes, tetrazaindenes (especially 4-hydroxy-substituted (1,3,3a,7)tetrazaindenes), pentazaindenes, etc.; benzenethiosulfonic acid, benzenesulfinic acid, benzenesulfonic amide, etc.; can be used. For example, the compounds as described in U.S. Pat. Nos. 3,954,474 and 3,982,947, Japanese Patent Publication No. 28660/77 can be used.

For the purpose of increasing sensitivity, increasing contrast, or accelerating development, the photographic emulsion layer(s) of the photographic light-sensitive element according to the present invention can contain other known additives, such as, for example, polyalkylene oxides or derivatives thereof such as ethers, esters, amines, etc., thioether compounds, thiomorpholine compounds, quaternary ammonium compounds, urethane derivatives, urea derivatives, imidazole derivatives, 3-pyrazolidones, etc. For example, such additives as described in U.S. Pat. Nos. 2,400,532, 2,423,549, 2,716,062, 3,617,280, 3,772,021, 3,808,003, British Pat. No. 1,488,991, etc.

The photographic emulsion of the present invention can also be spectrally sensitized with methine dyes of other dyes. Suitable dyes which can be employed include cyanine dyes, merocyanine dyes, complex cyanine dyes, complex mercocyanine dyes, holopolar cyanine dyes, hemicyanine dyes, styryl dyes, and hemioxonol dyes. Of these dyes, cyanine dyes, merocyanine dyes and complex merocyanine dyes are particularly useful. Any conventionally utilized nucleus for cyanine dyes, such as basic heterocyclic nuclei, is applicable to these dyes. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by condensing alicyclic hydrocarbon rings with these nuclei and nuclei formed by condensing aromatic hydrocarbon rings with these nuclei, that is, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc., are appropriate. The carbon atoms of these nuclei can also be substituted.

In addition to merocyanine dyes and complex merocyanine dyes, those with nuclei having a keto-methyl structure, 5- or 6-membered heterocyclic nuclei such as a pyrazolin-5-one nucleus, a thiohydantoin nucleus, a 2-thioxazolidin-2,4-dione nucleus, a thiazolidin-2,4-dione nucleus, a rhodanine nucleus, a thiobarbituric acid nucleus, and so forth may also be used.

Further useful sensitizing dyes include those described in German Pat. No. 929,080, U.S. Pat. Nos. 2,231,658, 2,493,748, 2,503,776, 2,519,001, 2,912,329, 3,656,959, 3,672,897, 3,694,217, 4,025,349 and 4,046,572, British Pat. No. 1,242,588, Japanese Patent Publication Nos. 14030/69 and 24844/77, and so forth.

These sensitizing dyes can be employed individually, and can also be employed in combination. A combination of sensitizing dyes is often used, particularly for the purpose of supersensitization.

Representative examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publication Nos. 4936/68 and 12375/78, and Japanese Patent Application (OPI) Nos. 110618/77 and 109925/77.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic ring group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, and the like, can be present. The combinations described in U.S. Pat. Nos. 3,615,613, 3,615,641, 3,617,295 and 3,635,721 are particularly useful.

The hydrophilic colloid layers of the light-sensitive material prepared according to the present invention can contain water-soluble dyes, such as filter dyes, for purposes of preventing certain irradiations or other purposes. Such dyes include oxonol dyes, hemioxonol dyes, styryl dyes, merocyanine dyes, cyanine dyes and azo dyes. Of these dyes, oxonol dyes, hemioxonol dyes and merocyanine dyes are especially useful. Specific examples of such dyes which can be employed are described, for example, in British Pat. Nos. 584,609 and 1,177,429, Japanese Patent Application (OPI) Nos. 85130/73, 99620/74, 114420/74 and 108115/77, and U.S. Pat. Nos. 2,274,782, 2,533,472, 2,956,879, 3,148,187, 3,177,078, 3,247,127, 3,540,887, 3,575,704, 3,653,905, 3,718,472, 4,071,312 and 4,070,352.

The photographic emulsion layers and other hydrophilic colloid layers of the light-sensitive material prepared in accordance with the present invention can contain whitening agents, such as stilbenes, triazines, oxazoles, coumarins, etc. These agents can be water-soluble or can also be employed as a dispersion of water-insoluble whitening agents. Specific examples of fluorescent whitening agents are described in U.S. Pat. Nos. 2,632,701, 3,269,840 and 3,359,102, and British Pat. Nos. 852,075 and 1,319,763.

In the practice of the present invention, known color fading preventing agents as described below can be employed. These fading preventing agents can be used individually or in a combination of two or more thereof. Specific examples of known color fading preventing agents include, for example, hydroquinone derivatives as described in U.S. Pat. Nos. 2,360,290, 2,418,613, 2,675,314, 2,701,197, 2,704,713, 2,728,659, 2,732,300, 2,735,765, 2,710,801 and 2,816,028, British Pat. No. 1,363,921; gallic acid derivatives as described in U.S. Pat. Nos. 3,457,079 and 3,069,262; p-alkoxyphenols as described in U.S. Pat. Nos. 2,735,765 and 3,698,909, Japanese Patent Publication Nos. 20977/74 and 6623/77; p-oxyphenol derivatives as described in U.S. Pat. Nos. 3,432,300, 3,573,050, 3,574,627 and 3,764,337, Japanese Patent Application (OPI) Nos. 35633/77, 147434/77 and 152225/77; and bisphenol derivatives as described in U.S. Pat. No. 3,700,455, and so forth.

Light-sensitive elements prepared according to the present invention can also contain, as color fog preventing agents, hydroquinone derivatives, aminophenol derivatives, gallic acid derivatives, ascorbic acid derivatives, or the like. Specific examples of these agents are described in U.S. Pat. Nos. 2,360,290, 2,336,327, 2,403,721, 2,418,613, 2,675,314, 2,701,197, 2,704,713, 2,728,659, 2,732,300 and 2,735,765, Japanese Patent Application (OPI) Nos. 92988/75, 92989/75, 93928/75, 110337/75 and 146235/77, Japanese Patent Publication No. 23813/75, and so forth.

The present invention is also applicable to multilayer multicolor photographic materials containing layers sensitive to at least two different spectral wavelength ranges on a support. A multilayer color photographic material generally possesses at least one red-sensitive silver halide emulsion layer, at least one green-sensitive silver halide emulsion layer, and at least one blue-sensitive silver halide emulsion layer, respectively, on a support. The order of these layers can be varied if desired. Ordinarily, a cyan-forming coupler is present in a red-sensitive emulsion layer, a magenta-forming coupler is present in a green-sensitive emulsion layer, and a yellow-forming coupler is present in a blue-sensitive emulsion layer, respectively. However, if desired, different combinations can be employed.

In the photographic sensitive materials produced according to the present invention, the photographic emulsion layers and other layers are produced by applying to flexible bases such as conventionally used plastic films, paper, cloth, etc. or rigid bases such as glass, porcelain, metal, etc. As useful elastic bases, there are films composed of semisynthetic or synthetic high molecular materials such as cellulose nitrate, cellulose acetate, cellulose acetate butyrate, polystyrene, polyvinyl chloride, polyethylene terephthalate, polycarbonate, etc. and papers to which a baryta layer or α-olefin polymer (for example, polyethylene, polypropylene or ethylene-butene copolymer) is applied or laminated. The bases may be colored with dyes or pigments. In order to intercept light, the bases may be blackened. The surface of these bases is generally subjected to an undercoating treatment in order to improve adhesion to the photographic emulsion, etc. The surface of the bases may be subjected to corona discharging, ultraviolet ray application, flame treatment, etc., before or after the undercoating treatment. Further, the present invention can be used for color photosensitive materials comprising a layer having low oxygen permeability (for example, a layer composed of polyvinyl alcohol or homopolymer or copolymer of acrylonitrile, etc.) between the base and the photographic emulsion.

Known methods can be used for processing the light-sensitive material according to the present invention. Known processing solutions can be used. The processing temperature can be between about 18° C. and about 50° C., in general, but temperatures lower than about 18° C. or higher than about 50° C. may be used, if desired. Either a development processing for forming silver images used in a color reversal photographic processing or a color photographic processing comprising developing processing for forming dye images can be employed, as desired.

The color developer generally comprises an alkaline aqueous solution containing a color developing agent. Suitable color developing agents which can be employed include known primary aromatic amine developing agents, e.g., phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfamidoethylaniline, 4-amino-3-methyl-N-ethyl-N-β-methoxyethylaniline, etc.).

In addition, developing agents described in L.F.A. Mason, *Photographic Processing Chemistry*, at pages 226 to 229, Focal Press (1966), U.S. Pat. Nos. 2,193,015 and 2,592,364, Japanese Patent Application (OPI) No. 64933/73, etc., can be employed.

The color developers can also contain pH buffering agents, such as sulfites, carbonates, borates and phosphates of alkali metals, developing inhibitors or antifogging agents such as bromides, iodides, organic antifogging agents, etc. In addition, if desired, the color developers can also contain water softeners, preservatives such as hydroxylamine; organic solvents such as benzyl alcohol, diethylene glycol, etc.; developing accelerators such as polyethylene glycol, quaternary ammonium salts, amines; dye-forming couplers; competing couplers; fogging agents such as sodium borohydride; auxiliary developers such as 1-phenyl-3-pyrazolidone; viscosity-imparting agents; polycarboxylic acid type chelating agents described in U.S. Pat. No. 4,083,723; antioxidizing agents as described in German Patent Application (OLS) No. 2.622,950; and other known photographic developing additives.

The photographic emulsion layers after color development are generally bleach-processed. Bleach processing can be performed at the same time as fixing, or separately therefrom. Suitable bleaching agents which can be employed are compounds of polyvalent metals such as iron (III), cobalt (III), chromium (VI), copper (II), etc., peracids, quinones, nitroso compounds, etc. Specific examples include ferricyanides; bichromates; organic complexes of iron (III) or cobalt (III); aminopolycarboxylic acids such as ethylenediaminetetraacetic acid, nitrilotriacetic acid, 1,3-diamino-2-propanol tetraacetic acid, etc.; complexes of organic acids such as citric acid, tartaric acid, malic acid, etc.; persulfates; permanganates; nitrosophenol; etc.

It is advantageous that the couplers according to the present invention have excellent color forming properties when the light-sensitive material is treated with a bleaching solution or bleach-fixing solution having a weak oxidation power containing sodium ethylenediaminetetraacetate iron (III) and ammonium ethylenediaminetetraacetate iron (III). Ethylenediaminetetraacetate iron (III) complex is useful both in a bleaching solution and in a mono bath bleach-fixing solution.

Bleaching and bleach-fixing solutions can contain various additives, including bleach accelerating agents as described in U.S. Patents 3,042,520 and 3,241,966, Japanese Patent Publication Nos. 8506/70 and 8836/70, thioether compounds as described in Japanese Patent Application (OPI) No. 65732/78, and the like.

The present invention is explained in greater detail with reference to the example below, but the present invention should not be construed as being limited thereto.

EXAMPLE

A solution prepared by heating, at 50° C., a mixture of 10 g of 6-[2-(2,4-di-tert-amylphenoxy)butanamido]-5-hydroxy-3,4-dihydrocarbostyryl [Coupler (1)], 10 g of trioctyl phosphate, 20 ml of ethyl acetate and 10 ml of dimethylformamide was added to 100 ml of an aqueous solution containing 10 g of gelatin and 0.4 g of sodium dodecylbenzenesulfonate with stirring. The mixture was then passed 5 times through a preheated colloid mil, by which the coupler was finely dispersed together with the solvents.

The whole amount of the dispersion thus prepared was added to 400 g of a photographic emulsion containing 18 g of silver chlorobromide (bromide content: 30 mol%) and 15 g of gelatin and to the mixture, 25 ml of a 2% aqueous solution of 4,6-dichloro-2-hydroxytriazine as a hardener was added. The pH of the mixture was adjusted to 6.0 and coated on a cellulose triacetate film base to obtain a dry thickness of 7.0 microns. This was designated as Sample A.

In place of Coupler (1) described above, using the equimolar amount of Couplers (2), (6), (8), (11), (15), and (18) according to the present invention, films were prepared in an analogous manner as described above for Sample A, and designated as Samples B, C, D, E, F, and G, respectively.

For comparison, using the equimolar amount of Comparison Couplers (101), (102), (103) and (104) described below in place of Coupler (1) described above, films designated as Samples H, I, J and K, respectively, were prepared in an analogous manner as described for Sample A.

Comparison Coupler (101)

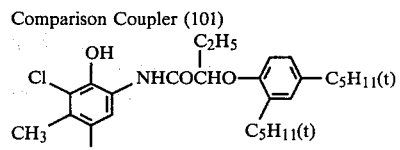

Comparison Coupler (102)

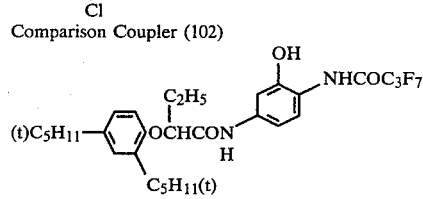

Comparison Coupler (103)

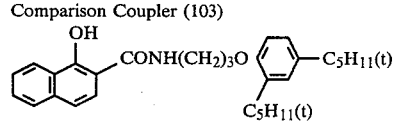

Comparison Coupler (104)

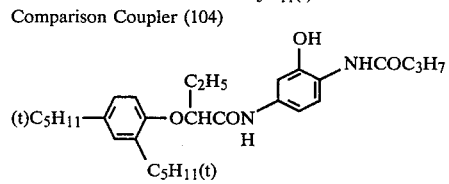

These films were exposed continuously using a sensitometric wedge and subjected to the following processing steps.

| Processing step | Temperature (°C.) | Time |
|---|---|---|
| 1. Color development | 33 | 3 min. 30 sec. |
| 2. Bleach-fixing | 33 | 1 min. 30 sec. |
| 3. Washing with water | 25 to 30 | 2 min. 30 sec. |

Each of the processing solutions used had the following composition.

| Color Developer Solution | |
|---|---|
| Benzyl Alcohol | 15 ml |
| Diethylene Glycol | 8 ml |
| Ethylenediaminetetraacetic Acid | 5 g |
| Sodium Sulfite | 2 g |
| Anhydrous Potassium Carbonate | 30 g |
| Hydroxylamine Sulfate | 3 g |
| Potassium Bromide | 0.6 g |
| 4-Amino-N-ethyl-N-(β-methanesulfonamidoethyl)-m-toluidine Sesquisulfate Monohydrate | 5 g |
| Water to make | 1 l |
| (pH 10.2) | |

| Bleach-Fixing Solution | |
|---|---|
| Ethylenediaminetetraacetic acid Ferric Salt of | 2 g |
| Ethylenediaminetetraacetate | 40 g |
| Sodium Sulfite | 5 g |
| Ammonium Thiosulfate | 70 g |
| Water to make | 1 l |

Each film thus processed was subjected to testing with respect to (1) fastness to light, (2) fastness to heat, and (3) fastness to humidity and heat. More particularly, in Test (1) the samples were irradiated for 6 days in a Xenon-lamp test apparatus (100,000 luxes), in Test (2) the samples were left for 6 days in a dark place at 100° C., and in Test (3) the samples were left for 6 weeks in a dark place at 60° C. and 70%RH, a density reduction rate of the sample in the area where initial density was 1.0 was measured. The results obtained are shown in Table 1.

TABLE 1

| Film Sample | Coupler | % Fading (based on original density) | | |
|---|---|---|---|---|
| | | Test (1) (Xenon Light) | Test (2) (100° C.) | Test (3) (60° C., 70% RH) |
| A | (1) Present Invention | 8% | 0% | 4% |
| B | (2) Present Invention | 18% | 4% | 6% |
| C | (6) Present Invention | 16% | 6% | 7% |
| D | (8) Present Invention | 19% | 6% | 8% |
| E | (11) Present Invention | 18% | 6% | 8% |
| F | (15) Present Invention | 12% | 2% | 5% |
| G | (18) Present Invention | 9% | 8% | 9% |
| H | (101) Comparison | 34% | 65% | 20% |
| I | (102) Comparison | 76% | 8% | 11% |
| J | (103) Comparison | 30% | 20% | 14% |
| K | (104) Comparison | 42% | 4% | 6% |

It is apparent from the results shown in Table 1 above that the dye images formed from the cyan couplers according to the present invention are extremely fast both to light and heat.

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive material comprising a support having coated thereon at least one silver halide emulsion layer, said photographic material containing a cyan dye forming coupler represented by formula (I)

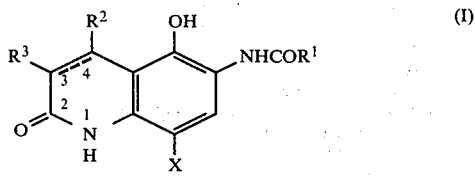

wherein $R^1$ represents a substituted or unsubstituted alkyl group or a substituted or unsubstituted aryl group; $R^2$ and $R^3$ each represents hydrogen, a halogen atom, an alkyl group, an aryl group, an alkoxy group, an alkoxycarbonyl group, an alkylcarbonyl group, an arylcarbonyl group, an alkylcarbamoyl group, an arylcarbamoyl group, wherein said groups may be substituted or unsubstituted, or a nitryl group; X represents hydrogen or a coupling-off group; and the bond between the carbon atom at the 3-position and the carbon atom at the 4-position may be a single or double bond.

2. A color photographic light-sensitive material as in claim 1, wherein said alkyl group represented by $R^1$ is an alkyl group having from 1 to 22 carbon atoms.

3. A color photographic light-sensitive material as in claim 1, wherein the substituents of the alkyl group or aryl group represented by $R^1$ are an alkyl group, a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, an acyloxy group, a sulfamoyl group, a carbamoyl group, an acylamino group, a diacylamino group, a ureido group, a sulfonamido group, or a hydroxy group.

4. A color photographic light-sensitive material as in claim 1, wherein said alkyl groups represented by $R^2$ and $R^3$ are alkyl groups having from 1 to 22 carbon atoms.

5. A color photographic light-sensitive material as in claim 1, wherein the substituents of the alkyl and aryl group represented by $R^2$ and $R^3$ are an alkyl group, a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, an acyloxy group, a sulfamoyl group, a carbamoyl group, an acylamino group, a diacylamino group, a ureido group, a sulfonamido group, or a hydroxy group.

6. A color photographic light-sensitive material as in claim 1, wherein X represents hydrogen.

7. A color photographic light-sensitive material as in claim 1, wherein X represents a halogen atom, an alkoxy group, an aryloxy group, an acyloxy group, a sulfonyloxy group, an acylamino group, a sulfonylamino group, an alkoxycarbonyloxy group, an aryloxycarbonyloxy group, or an imido group.

8. A color photographic light-sensitive material as in claim 1, wherein $R^1$ represents an alkyl group having from 8 to 22 carbon atoms or an aryl group having from 8 to 22 carbon atoms.

9. A color photographic light-sensitive material as in claim 1, wherein $R^2$ represents an alkyl group or a substituted phenyl group.

10. A color photographic light-sensitive material as in claim 1, wherein $R^3$ represents hydrogen or a halogen atom.

11. A color photographic light-sensitive material as in claim 1, wherein X represents a chlorine atom.

12. A color photographic light-sensitive material as in claims 1, 2, 3, 4, 5, 6, 7, 8, 9, 10, or 11, wherein said cyan dye forming coupler is present in a silver halide emulsion layer.

13. A color photographic light-sensitive material as in claim 12, wherein said silver halide emulsion layer is a red sensitive silver halide emulsion layer.

14. A color photographic light-sensitive material as in claim 13, wherein said cyan dye forming coupler is present in an amount of from about $2 \times 10^{-3}$ mol to $5 \times 10^{-1}$ mol per mol of silver in said silver halide emulsion layer.

15. A color photographic light-sensitive material as in claim 13, wherein said photographic material further includes a blue sensitive silver halide emulsion layer and a green sensitive silver halide emulsion layer.

16. A color photographic light-sensitive material as in claim 15, wherein said blue sensitive silver halide emulsion layer contains a yellow color forming coupler and said green sensitive silver halide emulsion contains a magenta color forming coupler.

17. A color photographic light-sensitive material as in claim 13, wherein said cyan dye forming coupler is present in an amount of from $1 \times 10^{-2}$ mol to $5 \times 10^{-1}$ mol per mol of silver in said silver halide emulsion layer.

* * * * *